United States Patent
Walker et al.

(10) Patent No.: US 7,970,464 B2
(45) Date of Patent: Jun. 28, 2011

(54) METHOD AND SYSTEM FOR RESPONDING TO NON-PERFUSING AND NON-SHOCKABLE HEART RHYTHMS

(75) Inventors: Robert G Walker, Bothell, WA (US); James M Owen, Redmond, WA (US)

(73) Assignee: Physio-Control, Inc., Redmond, WA (US)

( * ) Notice: Subject to any disclaimer, the term of this patent is extended or adjusted under 35 U.S.C. 154(b) by 1029 days.

(21) Appl. No.: 11/591,194

(22) Filed: Oct. 31, 2006

(65) Prior Publication Data

US 2010/0094365 A9    Apr. 15, 2010

Related U.S. Application Data

(63) Continuation-in-part of application No. 10/713,177, filed on Nov. 13, 2003, now abandoned.

(60) Provisional application No. 60/426,122, filed on Nov. 13, 2002.

(51) Int. Cl.
*A61N 1/00* (2006.01)
*A61H 31/00* (2006.01)

(52) U.S. Cl. .............. 607/5; 607/4; 607/14; 601/41

(58) Field of Classification Search ............ 601/41; 607/5, 4, 14
See application file for complete search history.

(56) References Cited

U.S. PATENT DOCUMENTS

| | | | | |
|---|---|---|---|---|
| 5,090,418 A | * | 2/1992 | Squires et al. | 600/515 |
| 5,355,889 A | * | 10/1994 | Nevo et al. | 600/484 |
| 5,456,261 A | * | 10/1995 | Luczyk | 600/515 |
| 5,819,007 A | * | 10/1998 | Elghazzawi | 706/46 |
| 5,833,621 A | * | 11/1998 | Panescu et al. | 600/509 |
| 2001/0047140 A1 | * | 11/2001 | Freeman | 601/41 |
| 2002/0165585 A1 | * | 11/2002 | Dupelle et al. | 607/5 |
| 2003/0144701 A1 | | 7/2003 | Mehra | |
| 2004/0138713 A1 | * | 7/2004 | Stickney et al. | 607/5 |
| 2005/0267536 A1 | * | 12/2005 | Freeman et al. | 607/5 |

* cited by examiner

*Primary Examiner* — Niketa I Patel
*Assistant Examiner* — Nicole F Lavert
(74) *Attorney, Agent, or Firm* — Shumaker & Sieffert, P.A.

(57) ABSTRACT

A system and method are disclosed for prompting emergency medical personnel who are attending to a patient. When the patient presents a heart rhythm that is a non-perfusing and non-shockable rhythm or perfusing but unstable, the attending personnel are prompted to administer therapy, such as reestablishing perfusion by performing CPR. The attending personnel may also be urged to defer taking the pulse of the patient.

35 Claims, 2 Drawing Sheets

METHOD AND SYSTEM FOR RESPONDING TO NON-PERFUSING AND NON-SHOCKABLE HEART RHYTHMS

CROSS REFERENCES AND RELATED APPLICATION

This application is a continuation-in-part of U.S. application Ser. No. 10/713,177, filed Nov. 13, 2003, now abandoned, which claims the benefit of U.S. Provisional Application Ser. No. 60/426,122, filed on Nov. 13, 2002.

TECHNICAL FIELD

The invention relates to emergency medical devices, and more particularly, to medical devices or methods for treating cardiac conditions based on electrocardiogram analysis.

BACKGROUND

When a patient experiences a medical emergency, trained medical personnel may be summoned to provide emergency care. The medical personnel evaluate the condition of the patient and provide emergency treatment to restore a life sustaining condition and attempt to stabilize the patient.

When the patient has abruptly lost consciousness, the medical personnel check the patient's ECG and check for other vital signs such as the patient's pulse to determine whether the heart is perfusing, i.e., whether the heart is effectively pumping blood in a manner that will sustain the vital organs. The heart's stroke volume and rate are among the factors, which determine whether perfusion is adequate. Medical conditions such as ventricular fibrillation (VF), Ventricular Tachycardia (VT), or organized rhythms such as pulseless electrical activity (PEA) might be responsible for a failure of perfusion, which in turn might be responsible for the loss of consciousness. When the heart is not perfusing, the time required to determine and deliver the appropriate treatment is of great importance to the patient's chance of survival. The patient could die or suffer serious brain injury due to lack of oxygen unless perfusion is established promptly. Accordingly, it is important for the medical personnel to assess the condition of the patient promptly and take action that would benefit the patient.

Medical personnel typically bring an external defibrillator to the site of the emergency. The defibrillator may employ two or more electrodes to record an electrocardiogram (ECG). In addition, the defibrillator may prompt an operator, i.e., a person using the device and attending to the patient, to deliver a therapy to the patient based upon analysis of the physiological conditions of the patient.

When the heart of the patient is not perfusing, the cause of the non-perfusing rhythm could be VF, which may be responsive to defibrillation shock therapy. When shock therapy is to be applied, the medical personnel refrain from touching the patient, to avoid receiving an electric shock. When the heart of the patient is not perfusing for other reasons, however, the best course may be to reestablish perfusion by cardiopulmonary resuscitation (CPR) or other therapy that involves physical contact with the patient.

SUMMARY

Systems, methods and devices that expeditiously and efficiently prompts personnel attending to the patient to institute therapy to maintain perfusion when the patient presents an ECG rhythm that is unstable and that is non-shockable, or to reestablish perfusion when the patient presents an ECG rhythm that is not indicative of an organized perfusing rhythm and that is non-shockable are disclosed. A "non-perfusing" rhythm encompasses any rhythm that is not adequately perfusing, i.e., not adequate to sustain vital organs. Examples of non-perfusing rhythms include, but are not limited to, asystole, PEA, profound bradycardia, in which the patient exhibits a heart rate below a threshold capable of sustaining the vital organs, and a rhythm in which atrial electrical activity is present in the ECG, but ventricular electrical activity is not.

In some instances, the patient's heart rhythm upon analysis can be determined not to be a shockable rhythm. A "shockable rhythm" is a non-perfusing heart rhythm that can potentially be converted to a perfusing rhythm by administration of a therapeutic shock such as a defibrillation or cardioversion shock, and a "non-shockable rhythm" is a heart rhythm that cannot be converted to a perfusing rhythm by administration of a shock.

Conventional practice, such as decisions made by emergency medical personnel based on ALS, BLS AHA/ILCOR or other guidelines, may be to take the patient's pulse as the next stage of medical care. Such guidelines do not always address the specific physiologic condition of the patient and the decision making process can add delays to providing appropriate treatment that can adversely effect the patient's chances of survival. When the patient presents a rhythm that is non-perfusing and non-shockable, trying to find a pulse and obtain a pulse rate delays delivery of therapies that are of extreme importance to reestablishing perfusion. Such therapies may include, for example, CPR or administration of drugs to stimulate cardiac activity. Accordingly, when a non-shockable heart rhythm that is not indicative of a perfusing rhythm is identified, the disclosed system, method and device provide for prompting the personnel to begin applying therapy such as CPR immediately without first prompting to check the patient's pulse.

In an embodiment, a medical device such as an external defibrillator includes a processor that analyzes physiological signals, such as ECG signals, sensed via the defibrillation electrodes or other sensing devices. When the processor detects a non-shockable heart rhythm that is not indicative of a perfusing rhythm, the processor prompts the operator to begin CPR or other therapy based upon the physiological signals. The disclosed systems, methods and devices further support selection of a health care protocol as a function of the detected non-perfusing non-shockable heart rhythm. In general, health care protocols encompass plans, procedures and rules for treating patients, and depend upon the conditions of the patient.

One embodiment is directed to a method which includes detecting in a patient a heart rhythm and determining that the detected rhythm is a non-perfusing and a non-shockable rhythm. The method further includes prompting an operator to administer therapy, in response to the determination. The therapy can be, for example, CPR or drug therapy. The method can also include prompting the operator to defer taking a pulse of the patient. Another embodiment is directed to a computer-readable medium comprising instructions for causing a programmable processor to carry out such a method. Another embodiment is directed to a system that includes a sensor that detects electrical activity in a patient's heart; a user interface including an output device configured to deliver prompts to a user of the device; and a processor that is capable of receiving a signal indicative of the sensed electrical activity; analyzing the signal to determine if the heart rhythm is one of (a) a non-perfusing and-non-shockable rhythm and (b) a perfusing and unstable rhythm; and controlling the output device to prompt an operator to administer therapy in response to the determination.

Various of the disclosed embodiments may result in one or more advantages. When the processor determines that the patient is exhibiting a non-perfusing, non-shockable rhythm that could benefit from prompt administration of CPR or other non-shock therapy, the processor prompts the attending personnel to administer the therapy. Deferring a pulse check can result in a quicker administration of drugs or CPR or other therapy, and consequently a quicker reestablishment of perfusion, thereby reducing risks of injury due to oxygen deprivation. Medical personnel can save significant time and potentially make a substantial difference in the patient's survival or quality of life by administering the therapy immediately, and deferring taking the pulse until a later time.

Other advantages of the disclosed systems, methods and devices include enhancement of the ability to determine the best course of treatment for a patient who exhibits a shockable rhythm that follows a non-shockable rhythm, or vice-versa.

The details of one or more embodiments are set forth in the accompanying drawings and the description below. Other features, objects, and advantages will be apparent from the description and drawings, and from the claims.

DETAILED DESCRIPTION

Figure 1:
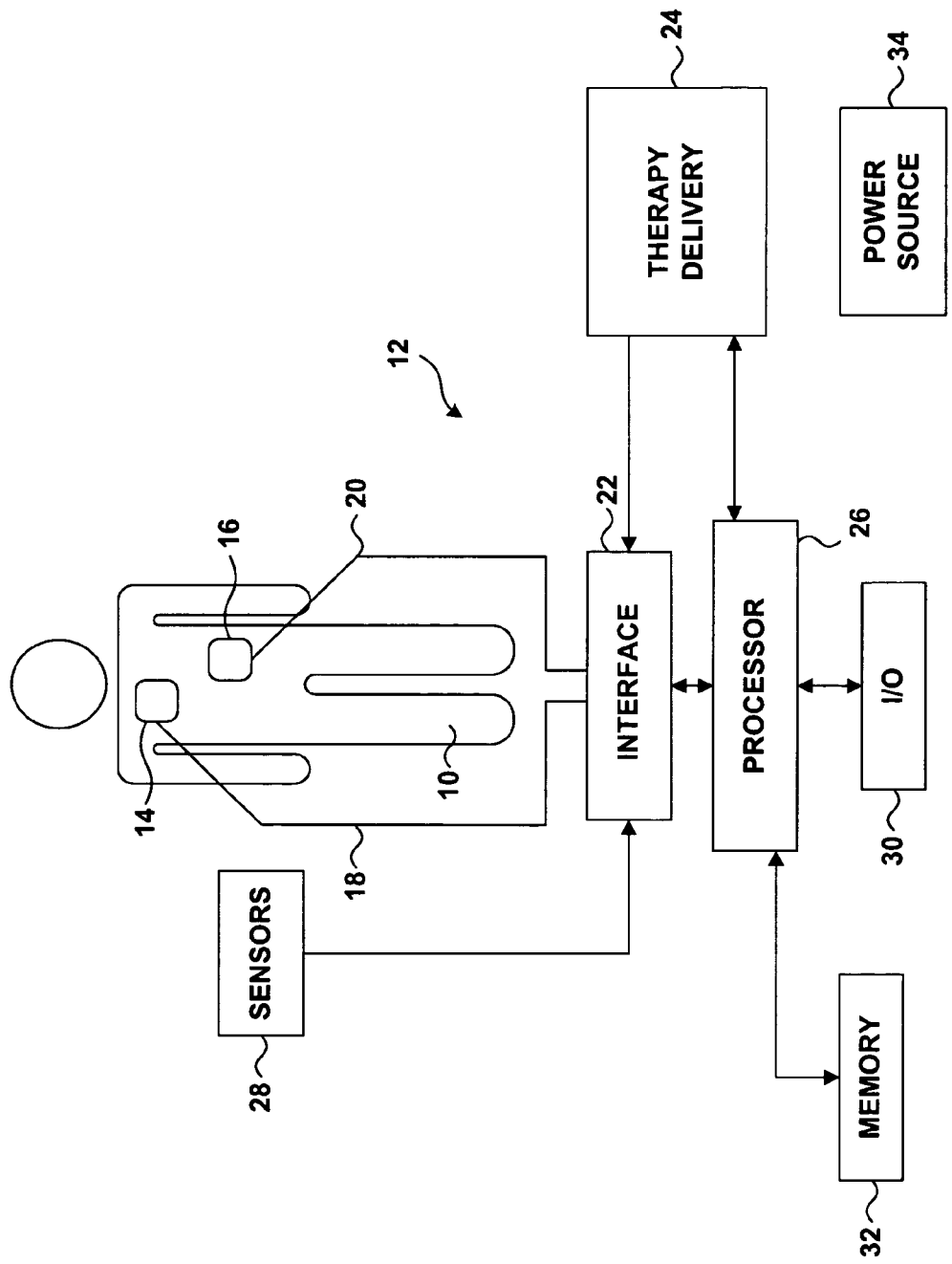
FIG. 1 is a schematic diagram of a defibrillator that may be used to practice techniques for responding to a non-perfusing, non-shockable heart rhythm according to an embodiment.

FIG. 1 is a block diagram illustrating a system according to an illustrative embodiment. A patient 10 is coupled to an external defibrillator 12. Although the embodiment will be described in the context of external defibrillator 12, external defibrillator 12 is one example of an emergency medical device that may be used to practice the disclosed systems, methods and devices. External defibrillator 12 can be an automated, semi-automated, or manual defibrillator. Other medical devices that can be used to practice the disclosed systems, methods and devices include, but are not limited to, a vital signs monitor, a patient care recorder, and a mechanical cardiopulmonary resuscitation (CPR) assist device.

Defibrillator 12 is configured to administer defibrillation therapy to patient 10 via electrodes 14 and 16, which may be hand-held electrode paddles or adhesive electrode pads placed externally on the skin of patient 10. The body of patient 10 provides an electrical path between electrodes 14 and 16.

Electrodes 14 and 16 are coupled to defibrillator 12 via conductors 18 and 20 and interface 22. In a typical application, interface 22 includes a receptacle, and connectors 18, 20 plug into the receptacle. Electrical impulses or signals may be sensed by defibrillator 12 via electrodes 14 and 16 and interface 22. Electrical impulses or signals may also be delivered from defibrillator 12 to patient 10 via electrodes 14 and 16 and interface 22, e.g., in the form of defibrillation shocks or pacing or cardioversion pulses.

Therapy delivery element 24 includes one or more modules configured to provide defibrillation therapy. Energy stored in therapy delivery element 24 can be delivered to patient 10 as a defibrillation shock, under the control of a processor 26, via electrodes 14 and 16. Interface 22, which operates under the control of processor 26, regulates when current may flow to patient 10, and may also regulate the direction of current flow.

Processor 26 may serve as a monitoring module that monitors the electrical activity in the heart of patient 10. For example, processor 26 may analyze electrical impulses or signals sensed via electrodes 14 and 16. In addition, processor 26 may analyze signals sensed via one or more sensors 28. Sensors 28 are configured to detect one or more physiological signals. Sensors 28 can include, for example, a set of electrocardiogram (ECG) leads that detect the electrical activity of the heart of patient 10. One embodiment could support a twelve-lead limb ECG electrode array, a three-wire lead array, or other array configured to measure an ECG. Processor 26 may, for example, apply algorithms to determine whether the ECG of patient 10 exhibits significant electrical activity of the heart, and whether the electrical activity is indicative of a normal heart rhythm or an arrhythmia. Processor 26 may further estimate the likely effectiveness of therapy for an arrhythmia. For example, processor 26 could carry out an analysis to determine whether a defibrillating shock would be effective therapy using methods described in, for example, U.S. patent application Ser. No. 11/095,305 filed on Mar. 31, 2005, U.S. Patent Application Publication No. 2004/0220489, or U.S. Pat. No. 6,438,419, all three of which are hereby incorporated by reference.

Processor 26 may determine in some cases that patient 10 is suffering from no arrhythmia, and in other cases, processor 26 may that patient 10 is suffering from ventricular fibrillation (VF). VF is one form of a non-perfusing rhythm, in that a heart experiencing VF contracts chaotically and in an uncoordinated fashion. Because a heart experiencing VF cannot perform a coordinated pumping action, the heart is unable to circulate blood and perfuse patient 10 in a manner that will sustain the patient's vital organs. VF is a "shockable" heart rhythm, that is, a heart rhythm that can be converted to a perfusing rhythm by administration of a therapeutic shock such as a defibrillation or cardioversion shock. Processor 26 is configured to detect VF and is further configured to determine that VF is a shockable heart rhythm.

There are other rhythms, distinct from VF, that are non-perfusing. Processor 26 can analyze signals from electrodes 14 and 16 or more sensors 28 to determine the presence of such non-perfusing rhythms. Some of the non-perfusing rhythms are "non-shockable." A non-shockable rhythm is a heart rhythm that cannot be converted to a perfusing rhythm by administration of a shock. Examples of non-perfusing, non-shockable heart rhythms are discussed below. Processor 26 is configured to determine whether the detected non-perfusing rhythm is a non-shockable rhythm.

When patient 10 is exhibiting a non-perfusing non-shockable arrhythmia, processor 26 can prompt or notify an operator that patient 10 should receive therapy directed to that arrhythmia. For example, processor 26 can prompt or notify an operator that patient 10 should promptly receive CPR. CPR helps reestablish perfusion and can improve the stability of the heart. As used herein, CPR encompasses chest compressions with or without ventilations of the patient. As another example, processor 26 can prompt or notify an operator as to an appropriate administration of CPR for patient 10, such as duration, number of chest compressions, and the like. Duration of the initial (or subsequent) CPR period can be adjusted based on an initial (or subsequent) ECG analysis. For example, the processor could prompt for a longer prompted period for CPR based upon the determination that the initial (or subsequent) ECG rhythm is asystole or PEA. As a further example, processor 26 can prompt or notify an operator that patient 10 should promptly receive a drug, such as vasopressors such as epinephrine, vasopressin, or antiarrythmic drugs such as amiodarone, and lidocaine, and other drug therapies used in resuscitation protocols.

Any prompts or notifications in the described embodiments may be in the form of an instruction, a command, an alerting signal or any other provision of information to the user. The notification provided to the operator of defibrillator 12 may be audible or visual. For example, one or more I/O devices 30 of defibrillator 12 may include an audio speaker, a display device, or both. Additional examples of I/O devices include but are not limited to a button, a keyboard, a touch screen, a voice recognition module, a pointing tool, a speaker, a display screen, an annunciator, and the like. Aural voiced prompts or text displays may be used to provide prompts, or the sounding of tones or other aural signals, or visual signals like colored or flashing lights, pictures, graphics, animations, video clips, or the like. An operator may interact with defibrillator 12 via I/O devices 30.

Processor 26 can, for example, determine that patient 10 is in asystole, i.e., the heart of patient 10 is exhibiting no ventricular electrical activity. Another example of a non-perfusing non-shockable arrhythmia is a low ventricular rate. Slow electrical complexes can indicate that the heart is not beating frequently enough so as to provide the cardiac output needed for perfusion of the vital organs. The threshold for whether a ventricular rate is low enough to be treated as a non-perfusing rhythm can be fixed number of beats per minute, such as thirty-five or forty beats per minute. Alternatively, a variable threshold can be applied to determine whether the ventricular rate is low enough to be considered as a non-perfusing rhythm. The threshold can vary depending upon the age, weight, physical fitness, or other characteristics of patient 10. For example, a higher beats-per-minute threshold, such as sixty beats per minute, may be applied when the patient is unconscious and unresponsive. Accordingly, in some embodiments, I/O device 30 may permit the operator to enter information one or more of such patient characteristics.

A further example of a non-perfusing non-shockable rhythm is pulseless electrical activity (PEA), in which electrical activity of the heart is unaccompanied by mechanical function.

The morphology of some ECG waveforms may indicate additional non-perfusing non-shockable rhythms, such as PEA. A broad QRS complex or other morphological characteristics could indicate poor perfusion or the absence of perfusion that could benefit from prompt and extended administration of CPR delivery of drug therapy, or both. Narrow and regular QRS complexes could indicate adequate perfusion or a cardiac condition that may soon become a perfusing rhythm. In this case, a shorter prompted period of CPR may be desirable. This may be followed by a patient assessments which may be indicated to the user by one or more prompts such as "check for pulse", "check for signs of circulation", "check for signs of respiration", or "check for signs of life", or other prompt suitable to instruct the user to assess the patient's condition. Processor 26 may apply one or more morphological analyses to the ECG to detect the presence of such non-perfusing, non-shockable rhythms. Morphological analyses could include, but are not limited to, Fourier analysis, wavelet analysis, pattern matching, and so forth.

R—R variability above a predetermined threshold, detection of a significant number of ectopic beats, an upward trend in R—R variability or number of ectopic beats, or the appearance of QRS complexes in bursts may, in some cases, indicate an unstable ECG rhythm that could benefit from prompt administration of drug therapy. Unstable ECG rhythms could indicate a non-perfusing condition, or a perfusing condition at higher risk of losing adequate perfusion. Detection of these conditions could also be used to determine the effectiveness of a drug therapy that had been administered to the patient or to determine the appropriate timing of when to administer additional drug therapy. Those skilled in the art will recognize that the threshold and trend characteristics that would indicate an indicate an unstable ECG rhythm that could benefit from prompt administration of drug therapy may vary from patient to patient, and will choose threshold levels or trend characteristics so as to achieve the desired clinical result.

Prompt administration of CPR can be of great significance to the patient. Seconds matter. If the patient is not perfusing, it is important to address that condition without undue delay. In the practices of some medical personnel, however, administration of CPR can be delayed following detection of a non-shockable rhythm while the personnel attempts to locate the pulse of the patient and measure the pulse. If the medical personnel are unable to locate the pulse at the neck of the patient, for example, the personnel may try to locate the pulse at the wrist or groin. Assuming a pulse is located, it will take several seconds to estimate the pulse rate. These pulse-checking efforts can take many seconds.

According to the illustrated embodiment, defibrillator 12 prompts the medical personnel to defer the taking of the patient's pulse when the patient exhibits a non-perfusing, non-shockable rhythm. In particular, processor 26 determines whether the rhythm is non-shockable and non-perfusing. When the patient exhibits a non-perfusing, non-shockable rhythm, taking the pulse is unlikely to provide information useful to understanding the condition of the patient. Further, CPR, drug therapy or other therapy should be administered immediately. Efforts to make a pulse measurement serve to delay administration of this therapy. Accordingly, defibrillator 12 can be configured to prompt the operator via I/O device 30 to begin therapy, such as CPR, right away. Defibrillator 12 can further be configured to prompt the operator via I/O device 30 not to take a pulse. Defibrillator 12 may prompt the operator not to take a pulse by omitting a pulse check prompt and instead progressing to the next prompt that is not a pulse check prompt. Alternatively, defibrillator 12 may prompt the operator to not check for pulse by issuing an explicit voiced or text prompt instructing the operator not to check for pulse such as "Do not check for pulse," or "Start CPR, do not check for pulse," an immediate "Start CPR" prompt, or the like.

Processor 26 may retrieve instructions pertaining to analysis and therapies, as well as other data, from memory 32. Memory 32 may include volatile storage, such as random access memory, and/or non-volatile storage, such as Flash memory or a hard disk. Memory 32 stores instructions that direct the operation of processor 26. In addition, memory 32 stores information about patient 10 and defibrillator 12. For example, memory 32 may store data relating to electrical signals sensed by defibrillator 12 and the response of patient 10 to therapy.

In addition, memory 32 may store information pertaining to one or more health care protocols. Health care protocols encompass plans, procedures and rules for treating patients, typically including information about tests, therapies and medications. Health care protocols encompass general procedures, as well as procedures applicable to a specific patient complaint, condition or presentation. Further, health care protocols include rules and guidelines pertaining to appropriate emergency care that are applicable in a particular jurisdiction. Defibrillator 12 can present information to the operator via I/O devices 30 pursuant to a health care protocol. The presented information may include sets of procedures, reference information and prompts to the operator for operations to be performed, such as CPR steps.

Defibrillator 12 includes a power source 34, which supplies the power for the electronic components of defibrillator 12 as well as the power for defibrillation shocks. Power source 34 may include an adapter to an exterior power source such as an electrical outlet, making defibrillator 12 "line-powered." In many situations, however, patient 10 may be far from an electrical outlet. Accordingly, power source 34 may comprise a battery, making defibrillator 12 portable and useful in a wider variety of emergency situations.

Figure 2:
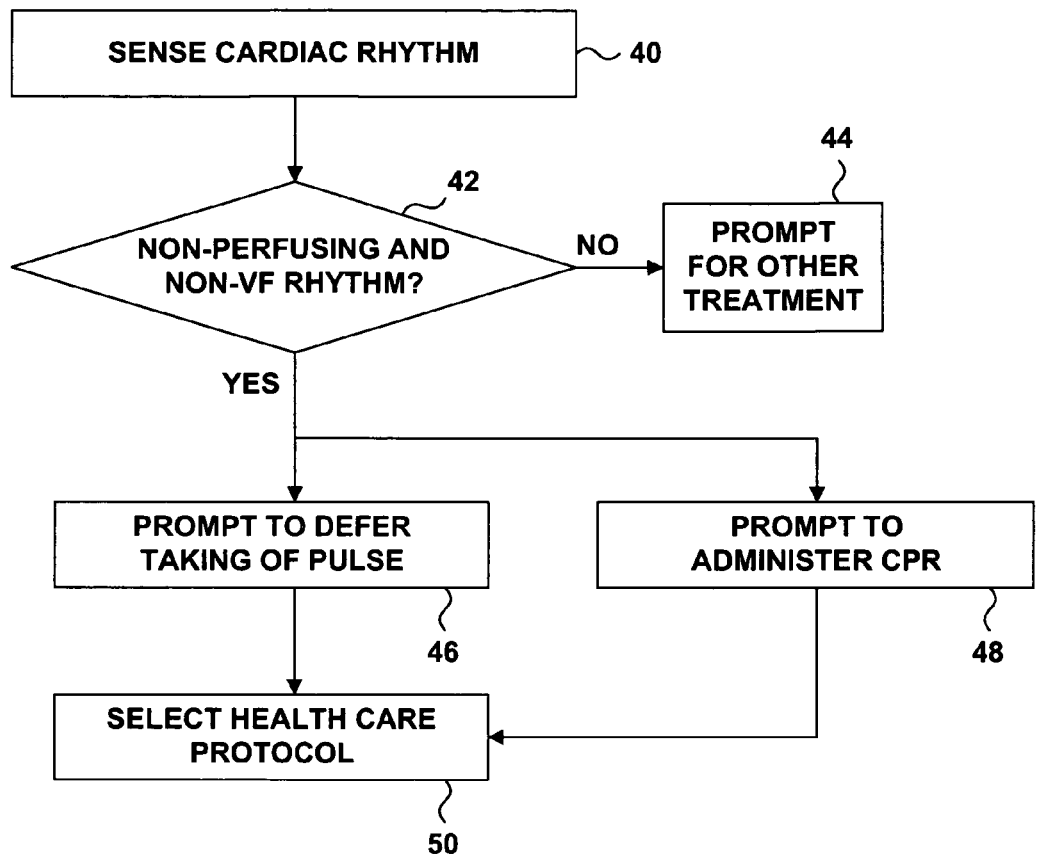
FIG. 2 is a flow diagram illustrating a procedure for responding to a non-perfusing, non-shockable heart rhythm.

FIG. 2 is a flow diagram illustrating an example of a procedure according to the illustrated embodiment that can be carried out by a processor, such as processor 26 of defibrillator 12. Processor 26 senses a cardiac rhythm (40) via electrodes 14 and 16 or sensors 28, and determines whether the patient exhibits a non-perfusing and non-shockable heart rhythm (42). In actual practice, it is possible that processor 26 may determine that the rhythm is non-shockable before determining that the rhythm is non-perfusing. In other words, in some embodiments the processor 26 may apply a longer analysis to non-shockable rhythms. Such an analysis can be useful when, for example, the patient exhibits a potentially unstable perfusing rhythm after regaining consciousness from a cardiac arrest. Should the rhythm become non-perfusing, processor 26 can prompt an operator to deliver drug therapy or CPR for conditions such as a short burst of ventricular tachycardia, R—R interval variability, significant numbers of ectopic beats, asystole, profound bradycardia, and so forth. The invention is not limited, however, to embodiments in which processor 26 determines whether or not the rhythm is a non-shockable rhythm first, and subsequently determines whether or not the rhythm is non-perfusing.

In the event the patient exhibits a shockable rhythm such as VF or no arrhythmia, defibrillator 12 can prompt the operator via I/O device 30 to provide therapy appropriate to the condition of the patient (44). In the event the patient exhibits a non-perfusing non-shockable rhythm, defibrillator 12 can prompt the operator via I/O device 30 to apply therapy, for example, to begin prompt administration of CPR (46). Optionally, defibrillator 12 can further prompt the operator via I/O device 30 not to spend time taking the patient's pulse (48).

As discussed previously, memory 32 may store information pertaining to one or more health care protocols, and processor 26 of defibrillator 12 can present information to the operator via I/O devices 30 pursuant to a health care protocol. When processor 26 determines that the patient exhibits a non-perfusing non-shockable rhythm (42), processor 26 can select a protocol applicable to the rhythm (50). Processor 26 may, for example, access a protocol in memory 32 pertaining to broad QRS complexes when the patient has a broad QRS complex, or may access a protocol pertaining to slow heartbeat when the patient presents slow electrical complexes. Defibrillator 12 can present information to the operator via I/O devices 30 pursuant to the selected health care protocol, and can also receive information pursuant to the selected health care protocol.

The procedures set forth in FIG. 2 can be repeated. In some cases, a patient may initially exhibit a non-shockable non-perfusing rhythm, such as asystole or a wide QRS complex that is bradycardic. Following non-shock therapy such as CPR, the patient may exhibit a non-perfusing shockable rhythm. The procedures set forth in FIG. 2 can also be performed following defibrillation therapy. In some cases, patient 10 exhibits a shockable rhythm such as VF, and accordingly receives one or more therapeutic shocks from defibrillator 12. The shocks may be arranged in a "shock stack," which is a sequence of consecutive shocks without intervening CPR (which may, in some instances, be of varying energy presented in order of increasing energy delivered to the heart).

The procedures set forth in FIG. 2 may be embodied as a computer-readable medium comprising instructions for processor 26. A "computer-readable medium" includes but is not limited to read-only memory, Flash memory and a magnetic or optical storage medium. Further, "computer-readable medium" may comprise a component of memory 32, or may be independent of memory 32. Processor 26 may be realized by one or more microprocessors, digital signal processors (DSPs), application specific integrated circuits (ASICs), field programmable logic arrays (FPGAs), or other equivalent integrated or discrete logic circuitry.

The illustrated embodiments and other embodiments may result in one or more benefits. When signals from electrodes 14 and 16 or sensors 28 show that the patient is exhibiting a non-perfusing non-shockable rhythm that could benefit from prompt administration of CPR or drugs or other non-shock therapy, they provide for urging medical personnel to administer the therapy first, and check the pulse later. Deferring a pulse check can result in a quicker administration of therapy. The savings of time may be about fifteen seconds to one minute, but when the patient is not perfusing, those few seconds can make a substantial difference to the patient's survival or quality of life.

Various embodiments of the invention have been described, but the invention is not limited to these particular embodiments. For example, the invention is described in terms of a portable defibrillator, but the invention can be embodied in another device, such as a portable ECG reader or a stand-alone device not configured to deliver defibrillation shocks. These and other embodiments are within the scope of the following claims.

What is claimed is:

1. A method comprising the steps of:
   detecting in a patient a heart rhythm;
   determining whether the detected rhythm is either (a) a non-shockable rhythm or (b) a shockable rhythm; and
   if the rhythm is a non-shockable rhythm, determining whether the non-shockable rhythm is either (i) a non-perfusing and non-shockable rhythm or (ii) a perfusing and unstable rhythm;
   in which if the detected rhythm is a shockable rhythm, the method further comprises delivering electrical therapy to the patient;
   in which if the detected rhythm is a non-shockable rhythm, the method further comprises prompting an operator to administer a therapy in response to the determined non-shockable rhythm.

2. The method of claim 1, wherein prompting the operator to administer therapy in response to the determined non-shockable rhythm includes prompting the operator to administer CPR.

3. The method of claim 1, wherein prompting the operator to administer therapy in response to the determined non-shockable rhythm includes prompting the operator to administer a drug to the patient.

4. The method of claim 1, further comprising prompting the operator to defer taking a pulse of the patient.

5. The method of claim 1, wherein determining whether the non-shockable rhythm is a non-perfusing and non-shockable rhythm comprises determining that the detected rhythm includes asystole.

6. The method of claim 1, wherein determining whether the non-shockable rhythm is a non-perfusing and non-shockable rhythm comprises determining that the detected rhythm includes a heart rate below a predetermined threshold.

7. The method of claim 6, wherein the threshold is substantially equal to or less than forty beats per minute.

8. The method of claim 1, wherein determining whether the non-shockable rhythm is a non-perfusing and non-shockable rhythm comprises determining that the detected rhythm is one chosen from the group consisting of pulseless electrical activity, asystole, profound bradycardia, and atrial electrical activity unaccompanied by ventricular electrical activity.

9. The method of claim 1, wherein delivering electrical therapy to the patient comprises delivering a defibrillation shock to the patient.

10. The method of claim 1, wherein prompting the operator to administer therapy comprises prompting the operator to administer CPR therapy for a period of time and choosing a duration of the prompted CPR period based on a determination made in an ECG analysis.

11. The method of claim 1, wherein determining whether the non-shockable rhythm is a non-perfusing and non-shockable rhythm comprises analyzing the detected rhythm for a morphological characteristic associated with a non-shockable and non-perfusing ECG rhythm.

12. The method of claim 1, wherein determining that the detected rhythm is a perfusing and unstable rhythm comprises determining that the detected rhythm includes R—R variability above a predetermined threshold, a significant number of ectopic beats, or an appearance of QRS complexes in bursts.

13. The method of claim 12, further comprising determining from the detected heart rhythm the effectiveness of an administered drug therapy.

14. The method of claim 12, further comprising determining a timing of delivery of additional drug therapy based on the detected heart rhythm.

15. The method of claim 1, further comprising:
selecting a health care protocol in response to the determined non-shockable rhythm; and
presenting information pursuant to the protocol to assist the operator attending to the patient.

16. A non-transitory computer readable storage medium for use with a system where a patient heart rhythm has been detected, the medium comprising instructions for causing a programmable processor to:
Determine whether the detected patient heart rhythm is either (a) a non-shockable rhythm or (b) a shockable rhythm, and if the rhythm is a non-shockable rhythm, determine whether the non-shockable rhythm is either (i) a non-perfusing and non-shockable rhythm of (ii) a perfusing and unstable rhythm; in which if the detected rhythm is a shockable rhythm, the instructions further cause the programmable processor to control delivery of electrical therapy to the patient;
and in which if the detected rhythm is a non-shockable rhythm, the instructions further cause the programmable processor to control an output device to prompt an operator to administer therapy in response to the determined non-shockable rhythm.

17. The medium of claim 16, wherein the instructions further cause the processor to:
select a health care protocol in response to the determined non-shockable rhythm; and
cause the output device to present information pursuant to the protocol to assist an operator attending to the patient.

18. The medium of claim 16, wherein the instructions to control an output device to prompt an operator to administer therapy cause the processor to cause the output device to instruct the operator to administer CPR to the patient.

19. The medium of claim 16, wherein the instructions to control an output device to prompt an operator to administer therapy cause the processor to cause the output device to instruct the operator to administer a drug to the patient.

20. A system comprising:
a sensor that detects electrical activity in a patient's heart;
an external defibrillator therapy delivery element;
a user interface including an output device configured to deliver prompts to a user of the device and
a processor configured to:
receive a signal indicative of the sensed electrical activity;
analyze the signal to determine if the heart rhythm is either (a) a non-shockable rhythm or (b) a shockable rhythm, and if the rhythm is a non-shockable rhythm, determine whether the non-shockable rhythm is either (i) a non-perfusing and non-shockable rhythm of (ii) a perfusing and unstable rhythm; in which if the detected rhythm is a shockable rhythm, the processor is capable of controlling the external defibrillation therapy delivery element to provide defibrillation therapy to the patient; and in which if the detected rhythm is a non-shockable rhythm the processor is configured to control the output device to prompt an operator to administer therapy in response to the determined non-shockable rhythm.

21. The system of claim 20, wherein the processor controls the output device to prompt the operator to administer CPR to the patient.

22. The system of claim 20, wherein the sensor comprises a twelve-lead limb ECG electrode array.

23. The system of claim 20, further comprising memory that stores a plurality of health care protocols,
wherein the processor is further configured to select a health care protocol from the plurality of health care protocols in the memory in response to the determined non-shockable rhythm, and is capable of controlling the output device to cause it to present information pursuant to the selected health care protocol to a user.

24. The system of claim 20, wherein the output device comprises one of a touch screen, a speaker, a display screen, or an annunciator.

25. The system of claim 20, wherein the processor is further configured to choose a duration of a prompted CPR period based on a determination made in an ECG analysis.

26. The system of claim 20, wherein the processor is further configured to determine whether the detected rhythm is a non-perfusing and non-shockable rhythm by analyzing the detected rhythm for a morphological characteristic associated with a non-shockable and non-perfusing ECG rhythm.

27. The system of claim 20, wherein the prompt is an instruction to administer a drug to the patient.

28. The system of claim 20, wherein the prompt is an instruction to defer taking a pulse of the patient.

29. The system of claim 20, wherein the processor is further configured to determine that the heart is in asystole.

30. The system of claim 20, wherein the processor is further configured to determine that a heart rate is below a predetermined threshold.

31. The system of claim 30, wherein the threshold is substantially equal to or less than forty beats per minute.

32. The system of claim 20, wherein the processor is configured to determine whether the detected rhythm is any one of pulseless electrical activity, asystole, profound bradycardia, and atrial electrical activity unaccompanied by ventricular electrical activity.

33. The system of claim 20, wherein the processor is further configured to determine that an ECG rhythm is unstable.

34. The system of claim 1, wherein the processor is further configured to determine that the heart rhythm includes any of R—R variability, an ectopic beat, or QRS complexes in bursts.

35. The system of claim 20, wherein the processor is further configured to determine from an ECG analysis the effectiveness of an administered drug therapy.

\* \* \* \* \*

UNITED STATES PATENT AND TRADEMARK OFFICE
CERTIFICATE OF CORRECTION

| | | |
|---|---|---|
| PATENT NO. | : 7,970,464 B2 | Page 1 of 1 |
| APPLICATION NO. | : 11/591194 | |
| DATED | : June 28, 2011 | |
| INVENTOR(S) | : Robert G. Walker and James M. Owen | |

It is certified that error appears in the above-identified patent and that said Letters Patent is hereby corrected as shown below:

In the Claims

On column 10, line 12, Claim 20, the words "an external defibrillator therapy delivery element" should read -- an external defibrillation therapy delivery element --;

On column 10, line 22, Claim 20, the words "...a non-perfusing and non-shockable rhythm of..." should read -- ...a non-perfusing and non-shockable rhythm or... --.

Signed and Sealed this
Thirtieth Day of July, 2013

Teresa Stanek Rea
*Acting Director of the United States Patent and Trademark Office*